United States Patent [19]

Schuetz et al.

[11] Patent Number: 4,952,720
[45] Date of Patent: Aug. 28, 1990

[54] ORTHO-SUBSTITUTED BENZYL CARBOXYLATES AND FUNGICIDES WHICH CONTAIN THESE COMPOUNDS

[75] Inventors: Franz Schuetz, Ludwigshafen; Hubert Sauter, Mannheim; Ulrich Schirmer, Heidelberg; Bernd Wolf, Mutterstadt; Eberhard Ammermann, Ludwigshafen; Ernst-Heinrich Pommer, Limburgerhof, all of Fed. Rep. of Germany

[73] Assignee: BASF Aktiengesellschaft, Ludwigshafen, Fed. Rep. of Germany

[21] Appl. No.: 254,696

[22] Filed: Oct. 7, 1988

[30] Foreign Application Priority Data

Oct. 7, 1987 [DE] Fed. Rep. of Germany ....... 3733870

[51] Int. Cl.[5] ............................................. C07C 69/76
[52] U.S. Cl. ...................... 560/106; 560/55; 560/60; 560/61; 549/562; 549/499; 558/390
[58] Field of Search ...................... 560/106, 55, 60, 61; 549/562, 499; 158/390

[56] References Cited

U.S. PATENT DOCUMENTS 4,709,078 11/1987 Schirmer et al. .
4,723,034 2/1988 Schirmer et al. .

FOREIGN PATENT DOCUMENTS 203606 12/1986 European Pat. Off. .
203608 12/1986 European Pat. Off. .
226917 7/1987 European Pat. Off. .
229974 7/1987 European Pat. Off. .
251082 1/1988 European Pat. Off. .
253213 1/1988 European Pat. Off. .

Primary Examiner—Paul J. Killos
Attorney, Agent, or Firm—Oblon, Spivak, McClelland, Maier & Neustadt

[57] ABSTRACT

Ortho-substituted benzyl carboxylates of the formula

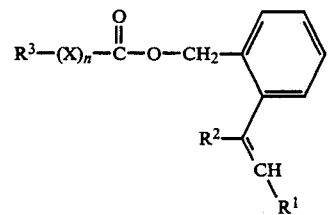

where $R^1$ is alkoxy, alkylthio, halogen or amino, $R^2$ is alkoxycarbonyl, cyano or $CONH_2$, $R^3$ is hydrogen, halogen, cyano, aryl, aryloxy, a saturated or unsaturated heterocyclic radical, cycloalkyl, or substituted cyclopropyl, X is alkylene, and n is 0 or 1, and fungicides containing these compounds.

6 Claims, No Drawings

ORTHO-SUBSTITUTED BENZYL CARBOXYLATES AND FUNGICIDES WHICH CONTAIN THESE COMPOUNDS

The present invention relates to novel ortho-substituted benzyl carboxylates and fungicides which contain these compounds.

It is known that N-tridecyl-2,6-dimethylmorpholine or methyl α-(2-benzoyloxyphenyl)-β-methoxyacrylate can be used as fungicides (DE 11 64 152 and EP No. 178 826). However, their fungicidal actions are unsatisfactory in some cases.

We have found that novel ortho-substituted benzyl carboxylates of the formula

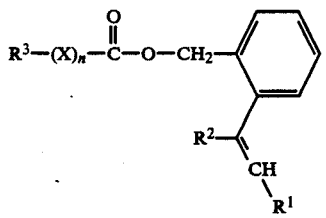

where $R^1$ is $C_1$–$C_4$-alkoxy, $C_1$–$C_4$-alkylthio or halogen or is amino which may be monosubstituted or disubstituted by $C_1$–$C_4$-alkyl, $R^2$ is $C_1$–$C_4$-alkoxycarbonyl, cyano or $CONH_2$, $R^3$ is hydrogen, halogen, cyano, aryl or aryloxy, in which the aromatic ring is unsubstituted or substituted by one or more of the following radicals: $C_1$–$C_6$-alkyl, $C_2$–$C_4$-alkenyl, $C_1$- or $C_2$haloalkenyl, $C_1$–$C_6$-alkoxy, $C_1$–$C_4$-alkoxy-$C_1$–$C_4$-alkyl, aryl, aryl-$C_1$- or $C_2$-alkyl, aryloxy, aryloxy-$C_1$–$C_4$-alkyl, aryloxy-$C_1$–$C_4$-alkoxy, haloaryloxy-$C_1$–$C_4$-alkoxy, halogen, halo-$C_1$–$C_4$-alkoxy, $C_1$–$C_4$-alkylthio, thiocyanato, cyano or nitro, or $R^3$ is a saturated or unsaturated heterocyclic radical, $C_3$–$C_7$-cycloalkyl, $C_5$- or $C_6$-cycloalkenyl, adamantyl, fluorenyl or a cyclopropyl radical which is substituted by methyl, halogen (chlorine or bromine), $C_1$- or $C_2$-haloalkyl (trifluoromethyl, tetrabromethyl or dichlorodibromoethyl), $C_3$- or $C_4$-alkenyl (methylvinyl or dimethylvinyl), $C_2$- or $C_4$-haloalkenyl (dichlorovinyl, dichlorobutadienyl, difluorovinyl or trifluoromethylvinyl), methoxycarbonyl-$C_3$- or $C_4$-alkenyl (methylmethoxycarbonylvinyl), cyclopentylidenemethyl, phenyl, halophenyl (chlorophenyl), $C_1$- or $C_2$-alkoxyphenyl (ethoxyphenyl) or $C_1$-$_C_4$-alkylphenyl (tert-butylphenyl), X is straight-chain or branched, unsaturated or saturated $C_1$–$C_{12}$-alkylene which is unsubstituted or substituted by halogen or hydroxyl, and n is 0 or 1, have an excellent fungicidal action.

The radicals shown in the general formula can have, for example, the following meanings: $R^1$ can be, for example, straight-chain or branched $C_1$–$C_4$-alkoxy (e.g. methoxy, ethoxy, n-propoxy, isopropoxy, n-butoxy, isobutoxy, sec-butoxy or tert-butoxy), $C_1$–$C_4$-alkylthio (e.g. methylthio, ethylthio, n-propylthio, isopropylthio, n-butylthio, isobutylthio, sec-butylthio or tertbutylthio), halogen (e.g. chlorine or bromine), or amino which is unsubstituted or monosubstituted or disubstituted by $C_1$–$C_4$-alkyl (e.g. amino, methylamino, methylethylamino, dimethylamino, diethylamino or diisopropylamino).

$R^2$ can be, for example, $C_1$–$C_4$-alkoxycarbonyl (e.g. methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl), cyano or $CONH_2$.

$R^3$ can be, for example, hydrogen, halogen (e.g. fluorine, chlorine or bromine), cyano, aryl (phenyl or naphthyl) or aryloxy (phenoxy), in which the aromatic ring may be substituted by one or more of the following radicals: $C_1$–$C_6$-alkyl (e.g. methyl, ethyl, n-propyl, isopropyl, n-butyl, isobutyl, sec-butyl, tert-butyl n-pentyl, isopentyl, sec-pentyl, tert-pentyl, neopentyl or hexyl), $C_2$–$C_4$-alkenyl (e.g. vinyl or allyl), $C_1$- or $c_2$-haloalkyl (e.g. difluoromethyl or trifluoromethyl), $C_1$–$C_6$-alkoxy (e.g. methoxy, ethoxy, isopropoxy or tert-butoxy), $C_1$–$C_4$-alkoxy-$C_1$–$C_4$-alkyl (e.g. methoxymethyl), aryl (e.g. phenyl), aryl-$C_1$–$C_2$-alkyl (e.g. benzyl), aryloxy (e.g. phenoxy), aryloxy-$C_1$–$C_4$-alkyl (e.g. phenoxymethyl or phenoxyethyl), aryloxy-$C_1$–$C_4$-alkoxy, haloaryloxy-$C_1$–$C_4$-alkoxy (e.g. phenoxymethoxy, phenoxyethoxy, phenoxypropoxy, 2-chlorophenoxyethoxy or 4-chlorophenoxyethoxy), halogen (e.g. fluorine, chlorine, bromine or iodine), halo-$C_1$–$C_4$-alkoxy (e.g. 1,1,2,2-tetrafluoroethoxy), $C_1$–$C_4$-alkylthio (e.g. methylthio), thiocyanato, cyano or nitro.

$R^3$ may furthermore be a saturated or unsaturated heterocyclic radical (e.g. furyl or pyrrolyl), $C_3$–$C_7$-cycloalkyl, $C_5$- or $C'_6$-cycloalkenyl (e.g. cyclopropyl, cyclobutyl, cycylpentyl, cyclopentenyl, cyclohexyl, cyclohexenyl or cycloheptyl), 1-adamantyl, 9-fluorenyl or a cyclopropyl radical which is substituted by methyl, halogen (chlorine or bromine), $C_1$- or $C_2$-haloalkyl (trifluoromethyl, tetrabromoethyl or dichlorodibromoethyl), $C_3$- or $C_4$-alkenyl (methylvinyl or dimethylvinyl), $C_2$–$C_4$-haloalkenyl (dichlorovinyl, dichlorobutadienyl, difluorovinyl or trifluoromethylvinyl), methoxycarbonyl-$C_3$- or $C_4$-alkenyl (methylmethoxycarbonylvinyl), cyclopentyldinemethyl, phenyl, halophenyl (e.g. fluorophenyl, chlorophenyl, bromophenyl or dichlorophenyl), $C_1$- or $C_2$-alkoxyphenyl (e.g. methoxyphenyl or ethoxyphenyl), or $C_1$–$C_4$-alkylphenyl (e.g. methylphenyl, ethylphenyl, butylphenyl or tert-butylphenyl), for example:

| | |
|---|---|
| 2,2-dimethyl-3-(2',2'-dimethylvinyl)-cyclopropyl | (A1) |
| 2,2-dimethyl-3-(2',2'-dichlorovinyl)-cyclopropyl | (A2) |
| 2,2-dimethyl-3-(2',2'-dibromovinyl)-cyclopropyl | (A3) |
| 2,2-dimethyl-3-(2'-trifluoromethyl-2'-chlorovinyl)-cyclopropyl | (A4) |
| 2,2-dichloro-3,3-dimethylcyclopropyl | (A5) |
| 2,2,3,3-tetramethylcycylpropyl | (A6) |
| 2,2-dimethyl-3-(2',2'-difluorovinyl)-cyclopropyl | (A7) |
| 2,2-dimethyl-3-(2'-trifluoromethyl-2'-fluorovinyl)-cyclopropyl | (A8) |
| 2,2-dimethyl-3-(2'-methyl-2'-methoxycarbonylvinyl)-cyclopropyl | (A9) |
| 2,2-dimethyl-3-(4',4'-dichlorobutadienyl)-cyclopropyl | (A10) |
| 2,2-dimethyl-3-(1'-bromo-2',2',2'-tribromoethyl)-cyclopropyl | (A11) |
| 2,2-dimethyl-3-(1'-bromo-2',2'-dichloro-2'-bromo-ethyl)-cyclopropyl | (A12) |
| 2,2-dimethyl-3-cyclopentadienylmethylcyclopropyl | (A13) |
| 1-(4'-ethoxyphenyl)-2,2-dichlorocyclopropyl | (A14) |
| 2,2-dimethyl-3-(4'-tert-butylphenyl)-cyclopropyl | (A15) |

The radical X shown in the general formula I can be, for example, straight-chain $C_1$–$C_{12}$-alkylene e.g. methylene, ethylene, propylene, butylene, pentylene, hexylene or heptylene), branched $C_1$–$C_{12}$-alkylene (methylmethylene, dimethylmethylene, ethylmethylene, n- or isopropylmethylene, methylethylene, methylpropylene, dimethylpropylene, ethylpropylene, methylbutylene, dimethylbutylene, ethylbutylene, n- or isopropylbutylene, methylpentylene, dimethylpentylene, trimethylpentylene, methylhexylene, dimethylhexylene, trimethylhexylene, ethylhexylene, n- or isopropylhexylene or methylheptylene), $C_2$–$C_8$-alkenylene (e.g. vinylene, allylene, methylallylene, butenylene or methylbutenylene), halogen-substituted $C_1$–$C_{12}$-alkylene (e.g. chloromethylene, dichloromethylene, fluoromethylen difluoromethylene, bromomethylene, dibromomethylene, chloroethylene, fluoroethylene, bromethylene, fluoropropylene, chloropropylene, bromopropylene, fluorobutylene, chlorobutylene or bromobutylene), halogen-substituted $C_2$–$C_4$-alkenylene, e.g. chlorovinylene or dichlorovinylene) or hydroxyl-substituted $C_1$–$C_8$-alkylene (e.g. hydroxymethylene or hydroxyethylene).

Where n is 0, $X_n$ is a single bond.

The novel compounds can be prepared, for example, by reacting an ortho-substituted benzyl bromide of the general formula III, where $R^1$ and $R^2$ have the above-mentioned meanings, with an alkali metal salt, alkaline earth metal salt or ammonium salt of a carboxylic acid of the formula II, where $R^3$, X and n have the above-mentioned meanings, in a solvent or diluent and with or without the addition of a catalyst to give the novel compounds.

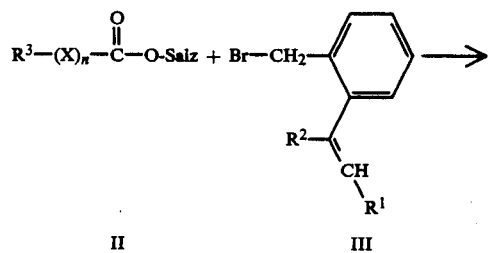

II    III

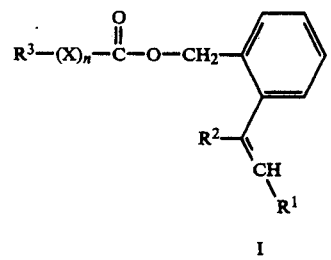

I

The preparation of carboxylic esters from alkyl halides and carboxylates is known per se (cf. for example Synthesis 1975, 805).

Suitable solvents or diluents for the reaction of II with III are acetone, acetonitrile, dimethyl sulfoxide, dioxane, dimethylformamide, N-methylpyrrolidone, N,N'-dimethylpropyleneurea and pyridine.

It may also be advantageous to add a catalyst, e.g. tetramethylethylenediamine, to the reaction mixture in an amount from 0.01 to 10% by weight, based on compound III.

The corresponding reactions can also be carried out in a two-phase system (e.g. carbon tetrachloride/water). Examples of suitable phase-transfer catalysts are trioctylpropylammonium chloride and cetyltrimethylammonium chloride (cf. Synthesis 1974, 867).

The carboxylates of the general formula II are obtained in a conventional manner from the corresponding carboxylic acids by reaction with bases (e.g. sodium hydroxide or potassium hydroxide) in an inert solvent (e.g. ethanol).

The carboxylic acids used are either known or can be prepared by processes similar to the known ones. Appropriate preparation processes are described in, for example, Chem. Ber. 119 (1986), 3694, Synthesis 1987, 738 and Angew. Chem. 93 (1981), 719.

The ortho-substituted benzyl bromides of the general formula III can be prepared, for example, by brominating an ortho-substituted toluene of the general formula IV with N-bromosuccinimide (Angew. Chem. 71 (1959), 349).

α-(2-Bromomethylphenyl)-acrylates of the general formula III (Where $R^1$ is alkoxy and $R^2$ is alkoxycarbonyl) are disclosed in DE Nos. -35 19 280, 35 45 318 and 35 45 319.

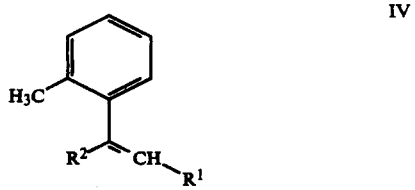

Because of their C=C double bond, the compounds of the general formula IV can occur both as E isomers and as Z isomers. The isomers can be separated in a conventional manner, for example by chromatography, fractional crystallization or distillation. The present invention relates to the individual isomeric compounds as well as their mixtures.

The compounds of the general formula IVa (where $R^1$ is alkoxy and $R^2$ is alkoxycarbonyl or cyano) are obtained from the hydroxymethylene derivatives of the general formula V, which may occur in equilibrium with the formyl derivatives VI, using an alkylating agent (e.g. dimethyl sulfate) in the presence of the base (e.g. potassium carbonate) in a diluent (e.g. acetone). In the formulae below, Alk is $C_1$–$C_4$-alkyl and X is a leaving group (e.g. methyl sulfate).

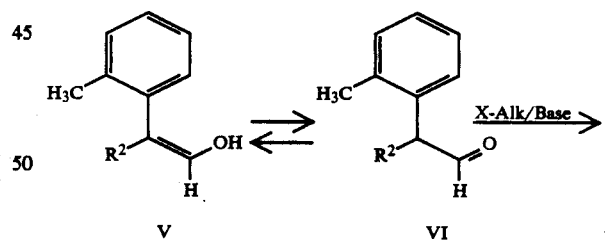

V    VI

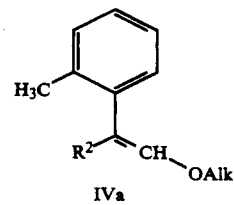

IVa $R^2$ = alkoxycarbonyl or cyano

For the preparation of the compounds of the general formula IVb (where $R^1$ is alkylthio and $R^2$ is alkoxycarbonyl or cyano), the hydroxymethylene derivatives V, which may also occur in equilibrium with VI, are first reacted with sulfonyl chlorides, e.g. methanesulfonyl chloride (R'=methyl), trifluoromethanesulfonyl chloride (R'=trifluoromethyl) or p-toluenesulfonyl chloride (R'=p-methylphenyl), in the presence of bases (e.g. triethylamine) to give compounds of the general formula VIII The desired compounds IVb are then obtained by reacting VII with alkyl thiolates AlkS⊖, e.g. sodium thiomethylate.

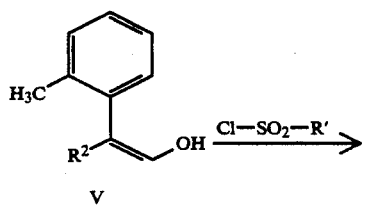

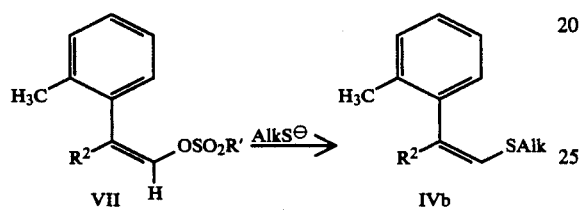

$R^2$ = alkoxycarbonyl or cyano

Compounds of the general formula IVc (where $R^1$ is halogen and $R^2$ is alkoxycarbonyl or cyano) are obtained by reacting a hydoxymethylene compound V, which may occur in equilibrium with the formyl derivatives VI, with an inorganic acid chloride (e.g. phosphorus pentachioride) (cf. for example Chem. Ber. 51 (1918), 1366).

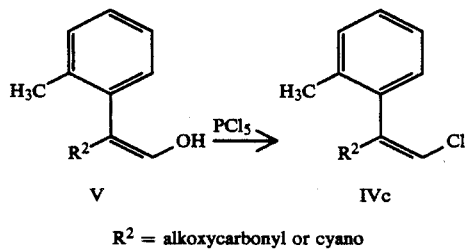

$R^2$ = alkoxycarbonyl or cyano

The compounds of the general formula IVd (where $R^1$ is alkylamino or dialkylamino and $R^2$ is alkoxycarbonyl or cyano) are prepared by reacting a hydroxymethylene derivative V, which may also occur in equilibrium with VI, with a primary or secondary amine. Alternatively, it is also possible to react the alkali metal salts of V with the hydrochlorides of primary or secondary amines with liberation of sodium chloride (cf. Ann. Chim. [10] 18 (1932) 103).

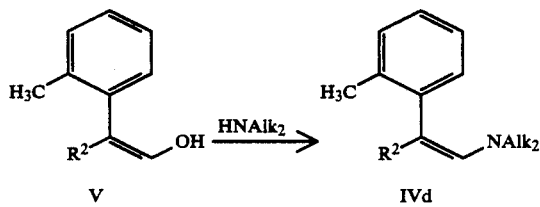

-continued
$R^2$ = alkoxycarbonyl or cyano

Compounds of the formula IVd are also obtained if an alkyl 2-methylphenylacetate VIII or 2-methylphenylacetonitrile IX is reacted with a dialkylformamide dialkyl acetal or with an aminal-alkyl ester (cf. for example Chem. Ber. 97 (1964), 3396).

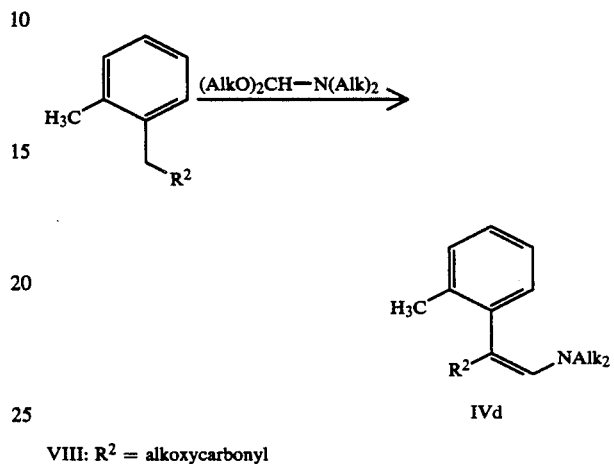

VIII: $R^2$ = alkoxycarbonyl
IX: $R^2$ = cyano

The novel compounds of the formula I where $R^2$ is $CONH_2$ are obtained starting from the corresponding derivatives in which $R^2$ is cyano, by alkaline hydrolysis (cf. Synthesis 1980, 243).

The hydroxymethylene derivatives of the general formula V which are required as starting compounds and in which $R^2$ is alkoxycarbonyl or cyano are obtained from an alkyl 2-methylphenylacetate VIII or from 2-methylphenylacetonitrile IX by reaction with methyl formate using a base (e.g. sodium hydride) in an inert solvent, e.g. diethyl ether or tetrahydrofuran (cf. Ann. Chem. 424 (1921), 214).

The Examples which follow illustrate the preparation of the novel active ingredients.

EXAMPLE 1

Methyl α-(2-benzoyloxymethylphenyl)-β-methoxyacrylate

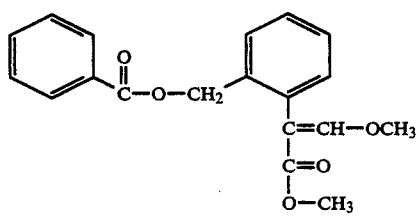

12.2 g (0.1 mole) of benzoic acid and 5.6 g (0.1 mole) of potassium hydroxide are dissolved in 150 ml of ethanol and the solution is stirred for 2 hours at room temperature (20° C.). The white precipitate which separates out is filtered off under suction, washed with diethyl ether and suspended in 300 ml of dimethylformamide. Thereafter, 28.5 g (0.1 mole) of methyl alpha-(2-bromomethylphenyl)-β-methoxyacrylate are added. The reaction mixture is then stirred for 24 hours at room temperature, after which it is evaporated down and the residue is taken up in methylene chloride. The organic phase is washed with water, dried over MgSO$_4$ and evaporated down. The oil obtained is chromatographed over silica gel using 10:1 cyclohexane/ethyl acetate. 25.4 g (78%) of the title compound are obtained as a colorless, viscous oil (compound No. 83).

EXAMPLE 2

Methyl α-[2-(1'-ortho-chlorophenyl)-cyclopropylcarbonyloxymethylphenyl]-β-methoxyacrylate

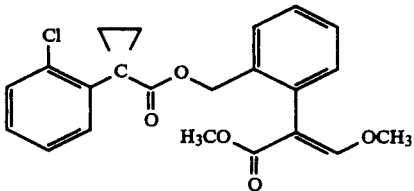

(a) A mixture of 30.0 g (200 millimoles) of 2-chlorobenzyl cyanide and 80.0 g (426 millimoles) of bromoethane are slowly added dropwise to a solution of 40.0 g of triethylbutylammonium chloride in 200 ml of 30% strength sodium hydroxide solution. The mixture is stirred for 2 hours at 80° C., allowed to cool, hydrolyzed with 500 ml of ice water and extracted with diethyl ether. The organic phase is washed with ammonium chloride solution and water, dried over MgSO$_4$ and evaporated down. The oil obtained is purified by distillation (97° C., 0.4 mbar). 20.0 g (56%) of 1-(2'-chlorophenyl)-cyclopropylnitrile are obtained as a colorless liquid.

(b) 11.0 g (62 millimoles) of 1-(2'-chlorophenyl)cyclopropylnitrile and 10.0 g (180 millimoles) of potassium hydroxide in 130 ml of diethylene glycol are refluxed for 2 hours. The mixture is allowed to cool, hydrolyzed with 200 ml of water and extracted with diethyl ether. The aqueous phase is acidified with dilute HCl and extracted with methylene chloride. The combined methylene chloride phases are dried over MgSO$_4$, evaporated down and covered with a layer of hexane. By means of trituration, 9.9 g (81%) of 1-(2'-chlorophenyl)-cyclopropanecarboxylic acid are obtained in the form of colorless crystals (mp.: 160° C.).

(c) 9.8 g (50 millimoles) of 1-(2'-chlorophenyl)cyclopropanecarboxylic acid and 2.8 g (50 millimoles) of potassium hydroxide are dissolved in 100 ml of ethanol and the solution is stirred for 1 hour at room temperature (20° C.). The white precipitate which separates out is filtered off under suction, washed with diethyl ether and suspended in 300 ml of N-methylpyrrolidone. Thereafter, 14.3 g (50 millimoles) of methyl α-(2-bromomethylphenyl)-β-methoxyacrylate are added. The mixture is stirred for 2 hours at 70° C., allowed to cool, hydrolyzed with 150 ml of water and extracted with methyl tert-butyl ether. The organic phase is washed with water, dried over MgSO$_4$ and evaporated down. The oil obtained is covered with a layer of hexane and crystallized by trituration. 12.8 (64%) of the title compound are obtained in the form of white crystals (mp.: 100°–101° C.).

The compounds below can be prepared in a similar manner:

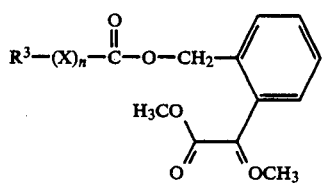

I

TABLE 1

Compounds of the formula I ($R^1$ = $OCH_3$, $R_2$ = $CO_2CH_3$)
The configuration statement relates to the β-methoxyacrylate group

| No. | $R^3$ | $(X)_n$ | Configuration | $^1$H-NMR data (CDd$_3$), δ in [ppm] | m.p. (°C.) |
|---|---|---|---|---|---|
| 1 | H | —CH$_2$— | E | 2.05(s,3H); 3.69(s,3H); 3.80(s,3H); 5.02(s,2H); 7.35(m,4H); 7.57(s,1H). | oil |
| 2 | H | —CH$_2$—CH$_2$— | E | | |
| 3 | H | —CH$_2$—CH(CH$_3$)— | E | | 74-75 |
| 4 | H | —CH$_2$—C(CH$_3$)$_2$— | E | | |
| 5 | H | —CH═CH— | E | | 61-62 |
| 6 | H | —CH═C(CH$_3$)— | E | | oil |
| 7 | H | —C≡C— | E | | |
| 8 | H | —CH$_2$—CH$_2$—CH$_2$— | E | | |
| 9 | H | —CH$_2$—CH$_2$—CH(CH$_3$)— | E | | oil |
| 10 | H | —CH$_2$—CH(CH$_3$)—CH$_2$— | E | | |
| 11 | H | —CH$_2$—CH$_2$C(CH$_3$)$_2$— | E | | |
| 12 | H | —CH$_2$—C(CH$_3$)$_2$—CH$_2$— | E | | |
| 13 | H | —CH$_2$—CH$_2$—C(C$_2$H$_5$)$_2$— | E | | |
| 14 | H | —CH═CH—CH$_2$— | E | | |
| 15 | H | —CH$_2$—CH═CH— | E | | |
| 16 | H | —CH$_2$—C(CH$_3$)═CH— | E | | |
| 17 | H | —CH$_2$—C═C(CH$_3$)— | E | | |
| 18 | H | —(CH$_2$)$_4$— | E | | oil |
| 19 | H | —CH$_2$—CH$_2$—CH$_2$—CH(CH$_3$)— | E | | |
| 20 | H | —CH$_2$—CH(CH$_3$)—CH$_2$—CH$_2$— | E | | |
| 21 | H | —(CH$_2$)$_3$—C(CH$_3$)$_2$— | E | | oil |
| 22 | H | —(CH$_2$)$_3$—CH(C$_2$H$_5$)— | E | | |
| 23 | H | —(CH$_2$)$_3$—CH(n-C$_3$H$_7$)— | E | | oil |
| 24 | H | —CH$_2$—CH═CH—CH$_2$— | E | | |
| 25 | H | —CH$_2$—C(CH$_3$)═CH—CH$_2$— | E | | oil |
| 26 | H | —(CH$_2$)$_5$— | E | | oil |
| 27 | H | —(CH$_2$)$_4$—CH(CH$_3$)— | E | | |
| 28 | H | —(CH$_2$)$_4$—CH(C$_2$H$_5$)— | E | | |
| 29 | H | —(CH$_2$)$_3$—CH(CH$_3$)—CH$_2$— | E | | |
| 30 | H | —CH$_2$—CH═CH—CH═CH— | E | | |
| 31 | H | —CH$_2$—C(CH$_3$)═CH—CH═CH— | E | | |
| 32 | H | —(CH$_2$)$_6$— | E | | |
| 33 | H | —(CH$_2$)$_5$—CH(CH$_3$)— | E | 0.88(t,3H); 0.93(d,3H); 1.29(m,4H); 1.96(m,1H); 2.13(m,1H); 2.33(m,1H); 3.69(s,3H); 3.79(s,3H); 5.03(s,2H); 7.32(m,4H); 7.57(s,1H). | |
| 34 | H | —(CH$_2$)$_4$—CH(CH$_3$)—CH$_2$— | E | | |
| 35 | H | —(CH$_2$)$_5$—CH(n-C$_3$H$_7$)— | E | | oil |
| 36 | H | —(CH$_2$)$_7$— | E | | |
| 37 | H | —(CH$_2$)$_6$—CH(CH$_3$)— | E | | |
| 38 | H | —(CH$_2$)$_5$—CH(CH$_3$)—CH$_2$— | E | | |
| 39 | H | —(CH$_2$)$_6$—C(CH$_3$)$_2$— | E | | |
| 40 | H | —(CH$_2$)$_8$— | E | | |
| 41 | H | —(CH$_2$)$_9$— | E | | |
| 42 | H | —(CH$_2$)$_{10}$— | E | | |
| 43 | H | —CHCl— | E | | |

TABLE 1-continued

Compounds of the formula I (R¹ = OCH₃, R² = CO₂CH₃)
The configuration statement relates to the β-methoxyacrylate group

| No. | R³ | (X)ₙ | Configuration | ¹H-NMR data (CDCl₃), δ in [ppm] | m.p. (°C.) |
|---|---|---|---|---|---|
| 44 | H | —CCl₂— | E | | |
| 45 | Cl | —CCl₂— | E | | |
| 46 | H | —CHBr— | E | | |
| 47 | H | —CBr₂— | E | | |
| 48 | Br | —CBr₂— | E | | |
| 49 | H | —CHF— | E | | |
| 50 | H | —CF₂— | E | | |
| 51 | F | —CF₂— | E | | |
| 52 | H | —CH=CCl— | E | | |
| 53 | H | —CCl=CCl— | E | | |
| 54 | Cl | —CCl=CCl— | E | | |
| 55 | Br | —C(CH₃)₂— | E | | |
| 56 | H | —C(CH₃)₂— | E | | |
| 57 | H | —CHCl—CH(CH₃)— | E | | |
| 58 | H | —CHCl—C(CH₃)₂— | E | | |
| 59 | Br | —CHBr—CH(CH₃)— | E | | |
| 60 | H | —C(C₂H₅)₂— | E | | |
| 61 | H | —CH(OH)— | E | | |
| 62 | H | —CH₂—CH(OH)— | E | | |
| 63 | H | —CH₂—CH₂—CH(OH)— | E | | |
| 64 | H | —CH₂—CH(OH)—CH₂— | E | | |
| 65 | H | —CH(OH)—CH₂— | E | | |
| 66 | H | —CH(OH)—C(CH₃)₂— | E | | |
| 67 | H | —CH₂—C(OH)(CH₃)— | E | | |
| 68 | H | —CH₂—CH(CH₃)—CH(OH)— | E | | |
| 69 | H | —CH=CH—CH(OH)— | E | | |
| 70 | H | —CH=CH—CH₂CH(OH)— | E | | |
| 71 | CN | —CH₂— | E | | |
| 72 | cyclopropyl | — | E | | |
| 73 | cyclobutyl | — | E | | oil |
| 74 | cyclopentyl | — | E | | |
| 75 | cyclohexyl | — | E | | |
| 76 | adamantyl | — | E | | |
| 77 | 9-fluorenyl | — | E | | oil |
| 78 | cyclopentyl | —CH₂— | E | | oil |
| 79 | 3-cyclopentenyl | —CH₂— | E | | oil |
| 80 | cyclohexyl | —CH₂— | E | | oil |
| 81 | cyclopentyl | —CH₂—CH₂— | E | | |
| 82 | cyclohexyl | —CH₂—CH₂— | E | | |
| 83 | cyclohexyl | —(CH₂)₃— | E | 3.60(s,3H); 3.76(s,3H); 5.27(s,3H); 7.50(m,9H); 7.57(s,1H). | |
| 84 | C₆H₅ (=phenyl) | — | E | | |
| 85 | 2-CH₃—C₆H₄ | — | E | | |
| 86 | 3-CH₃—C₆H₄ | — | E | | |
| 87 | 4-CH₃—C₆H₄ | — | E | | |
| 88 | 2,3-(CH₃)₂—C₆H₃ | — | E | | |
| 89 | 2,4-(CH₃)₂—C₆H₃ | — | E | | |
| 90 | 2,6-(CH₃)₂—C₆H₃ | — | E | | |
| 91 | 3,4-(CH₃)₂—C₆H₃ | — | E | | |
| | 3,5-(CH₃)₂—C₆H₃ | | | | |

TABLE 1-continued

Compounds of the formula I ($R^1$ = $OCH_3$, $R_2$ = $CO_2CH_3$)
The configuration statement relates to the β-methoxyacrylate group

| No. | $R^3$ | $(X)_n$ | Configuration | $^1$H-NMR data ($CDd_3$), δ in [ppm] | m.p. (°C.) |
|---|---|---|---|---|---|
| 92 | 2,4,6-$(CH_3)_3$—$C_6H_2$ | — | E | | |
| 93 | 4-t-$C_4H_9$—$C_6H_4$ | — | E | | |
| 94 | 2-$C_2H_5$—$C_6H_4$ | — | E | | |
| 95 | 4-$C_6H_5$—$C_6H_4$ | — | E | | |
| 96 | 2-benzyl-$C_6H_4$ | — | E | | |
| 97 | 4-benzyl-$C_6H_4$ | — | E | 3.65(s,3H); 3.83(s,3H); 5.30(s,2H); 7.55(m,8H); 7.63(s,1H). | oil |
| 98 | 2-Cl—$C_6H_4$ | — | E | | |
| 99 | 3-Cl—$C_6H_4$ | — | E | | |
| 100 | 4-Cl—$C_6H_4$ | — | E | | |
| 101 | 2,4-$Cl_2$—$C_6H_3$ | — | E | 3.62(s,3H); 3.73(s,3H); 5.27(s,2H); 7.48(m,7H); 7.68(s,1H). | oil |
| 102 | 2,5-$Cl_2$—$C_6H_3$ | — | E | | |
| 103 | 2,6-$Cl_2$—$C_6H_3$ | — | E | | |
| 104 | 3,4-$Cl_2$—$C_6H_3$ | — | E | | |
| 105 | 3,5-$Cl_2$—$C_6H_3$ | — | E | | |
| 106 | 2,4,5-$Cl_3$—$C_6H_2$ | — | E | | |
| 107 | 2,3,4,5,6-$Cl_5$—$C_6$ | — | E | | |
| 108 | 2-F-4-Cl—$C_6H_3$ | — | E | | 68-69 |
| 109 | 2-F—$C_6H_4$ | — | E | 3,3(s,3H); 3.73(s,3H); 5.29(s,2H); 7.49(m,8H); 7.60(s,1H); | 68-70 |
| 110 | 3-F—$C_6H_4$ | — | E | | oil |
| 111 | 4-F—$C_6H_4$ | — | E | | 63-65 |
| 112 | 2,4-$F_2$—$C_6H_3$ | — | E | | |
| 113 | 2,6-$F_2$—$C_6H_3$ | — | E | | |
| 114 | 2,3,4,5,6-$F_5$—$C_6$ | — | E | | |
| 115 | 2-$CF_3$—$C_6H_4$ | — | E | | oil |
| 116 | 3-$CF_3$—$C_6H_4$ | — | E | | |
| 117 | 4-$CF_3$—$C_6H_4$ | — | E | | |
| 118 | 2-$OCH_3$—$C_6H_4$ | — | E | | |
| 119 | 3-$OCH_3$—$C_6H_4$ | — | E | | |
| 120 | 4-$OCH_3$—$C_6H_4$ | — | E | | |
| 121 | 2-phenoxy-$C_6H_4$ | — | E | | |
| 122 | 3-phenoxy-$C_6H_4$ | — | E | | |
| 123 | 4-phenoxy-$C_6H_4$ | — | E | | |
| 124 | 4-ethoxy-$C_6H_4$ | — | E | | |
| 125 | 2-phenoxyethoxy-$C_6H_4$ | — | E | | |
| 126 | 2-(2'-Cl-phenoxyethoxy)-$C_6H_4$ | — | E | | |
| 127 | 2-(3'-Cl-phenoxyethoxy)-$C_6H_4$ | — | E | | |
| 128 | 2-(4'-Cl-phenoxyethoxy)-$C_6H_4$ | — | E | | |
| 129 | 3-phenoxyethoxy-$C_6H_4$ | — | E | | |
| 130 | 3-(4'-Cl-phenoxyethoxy)-$C_6H_4$ | — | E | | |
| 131 | 4-phenoxyethoxy-$C_6H_4$ | — | E | | |
| 132 | 2-phenoxypropoxy-$C_6H_4$ | — | E | | |
| 133 | 3-phenoxypropoxy-$C_6H_4$ | — | E | | |
| 134 | 4-phenoxypropoxy-$C_6H_4$ | — | E | | |
| 135 | $C_6H_5$ | —$CH_2$— | E | 3.59(s,2H); 3.63(s,3H); 3.65(s,3H); 7.28(m,9H); 7.52(s,1H). | oil |
| 136 | 2-$CH_3$—$C_6H_4$ | —$CH_2$— | E | | |
| 137 | $C_6H_5$ | —$CHCH_3$— | E | | |

TABLE 1-continued

Compounds of the formula I ($R^1$ = $OCH_3$, $R^2$ = $CO_2CH_3$)
The configuration statement relates to the β-methoxyacrylate group

| No. | $R^3$ | $(X)_n$ | Configuration | $^1$H-NMR data (CDd$_3$), δ in [ppm] | m.p. (°C.) |
|---|---|---|---|---|---|
| 138 | 4-phenyl-$C_6H_4$ | —$CH_2$— | E | | |
| 139 | 2-F—$C_6H_4$ | —$CH_2$— | E | | |
| 140 | 3-F—$C_6H_4$ | —$CH_2$— | E | | |
| 141 | 4-F—$C_6H_4$ | —$CH_2$— | E | | |
| 142 | 2-Cl—$C_6H_4$ | —$CH_2$— | E | | |
| 143 | 3-Cl—$C_6H_4$ | —$CH_2$— | E | | |
| 144 | 4-Cl—$C_6H_4$ | —$CH_2$— | E | | |
| 145 | 2,4-$Cl_2$—$C_6H_3$ | —$CH_2$— | E | | |
| 146 | 2,6-$Cl_2$—$C_6H_3$ | —$CH_2$— | E | | |
| 147 | 2-Cl-4-F—$C_6H_3$ | —$CH_2$— | E | | |
| 148 | 2-ethoxy-$C_6H_4$ | —$CH_2$— | E | | |
| 149 | 4-ethoxy-$C_6H_4$ | —$CH_2$— | E | | |
| 150 | 2-$OCH_3$—$C_6H_4$ | —$CH_2$— | E | | |
| 151 | 4-$OCH_3$—$C_6H_4$ | —$CH_2$— | E | | |
| 152 | 4-t-$C_4H_9$—$C_6H_4$ | —$CH_2$— | E | | |
| 153 | $C_6H_5$ | —CH(iso-$C_3H_7$)— | E | | |
| 154 | 4-Cl—$C_6H_4$ | —CH(iso-$C_3H_7$)— | E | 0.75(d,3H); 1.07(d,3H); 2.33(m,1H); 3.22(d,1H); 2.73(s,3H); 3.83(s,3H); 5.03(dd,2H); 7.35(m,8H); 7.58(s,1H). | oil |
| 155 | 4-F—$C_6H_4$ | —CH(iso-$C_3H_7$)— | E | | |
| 156 | 4-$OCF_2H$—$C_6H_4$ | —CH(iso-$C_3H_7$)— | E | | |
| 157 | $C_6H_5$ | —CH(OH)— | E | | |
| 158 | 2-$OCH_3$—$C_6H_4$ | —CH(OH)— | E | | |
| 159 | 3-$OCH_3$—$C_6H_4$ | —CH(OH)— | E | | |
| 160 | 4-$OCH_3$—$C_6H_4$ | —CH(OH)— | E | | |
| 161 | 4-Cl—$C_6H_4$ | —CH(OH)— | E | | |
| 162 | $C_6H_5$ | —CH($CH_2OH$)— | E | | |
| 163 | $C_6H_5$ | —$CH_2$—$CH_2$— | E | | |
| 164 | $C_6H_5$ | —CH($CH_3$)—$CH_2$— | E | | |
| 165 | $C_6H_5$ | —$CH_2$—CH($CH_3$)— | E | | |
| 166 | $C_6H_5$ | —CH($CH_3$)—CH($CH_3$)— | E | | |
| 167 | $C_6H_5$ | —CH($C_6H_5$)—$CH_2$— | E | 3.12(d,2H); 3.72(s,3H); 3.83(s,3H); 4.62(t,1H); 4.99(s,2H); 7.31(m,14H); 7.60(s,1H). | oil |
| 168 | 4-t-$C_4H_9$—$C_6H_4$ | —$CH_2$—$CH_2$— | E | | |
| 169 | 4-t-$C_4H_9$—$C_6H_4$ | —$CH_2$—CH($CH_3$)— | E | 1.16(d,3H); 1.30(s,9H); 2.72(m,2H); 3.02(m,1H); 3.70(s,3H); 3.82(s,3H); 5.00(s,2H); 7.18(m,8H); 7.60(s,1H). | oil |
| 170 | 2-Cl—$C_6H_4$ | —$CH_2$—$CH_2$— | E | | |
| 171 | 3-Cl—$C_6H_4$ | —$CH_2$—$CH_2$— | E | | |
| 172 | 4-Cl—$C_6H_4$ | —$CH_2$—$CH_2$— | E | | |
| 173 | 2-F—$C_6H_4$ | —$CH_2$—$CH_2$— | E | | |
| 174 | 3-F—$C_6H_4$ | —$CH_2$—$CH_2$— | E | | |
| 175 | 4-F—$C_6H_4$ | —$CH_2$—$CH_2$— | E | | |
| 176 | 2-$OCH_3$—$C_6H_4$ | —$CH_2$—$CH_2$— | E | | |
| 177 | 4-$OCH_3$—$C_6H_4$ | —$CH_2$—$CH_2$— | E | | |
| 178 | $C_6H_5$ | —CH=CH— | E | | |
| 179 | 2-Cl—$C_6H_4$ | —CH=CH— | E | 3.67(s,3H); 3.76(s,3H); 5.19(s,2H); 6.44(d,1h); 7.33(m,8H); 7.60(s,1H). | oil |

TABLE 1-continued

Compounds of the formula I ($R^1$ = $OCH_3$, $R^2$ = $CO_2CH_3$)
The configuration statement relates to the β-methoxyacrylate group

| No. | $R^3$ | $(X)_n$ | Configuration | $^1$H-NMR data ($CDd_3$), δ in [ppm] | m.p. (°C) |
|---|---|---|---|---|---|
| 180 | 3-Cl—$C_6H_4$ | —CH=CH— | E | 8.09(d,1H). | |
| 181 | 4-Cl—$C_6H_4$ | —CH=CH— | E | | |
| 182 | 2,6-$Cl_2$—$C_6H_3$ | —CH=CH— | E | | |
| 183 | 2,4-$Cl_2C_6H_3$ | —CH=CH— | E | | oil |
| 184 | 2-F—$C_6H_4$ | —CH=CH— | E | | |
| 185 | 3-F—$C_6H_4$ | —CH=CH— | E | | |
| 186 | 4-F—$C_6H_4$ | —CH=CH— | E | | |
| 187 | 2-$CF_3$—$C_6H_4$ | —CH=CH— | E | | oil |
| 188 | 4-$CF_3$—$C_6H_4$ | —CH=CH— | E | | oil |
| 189 | 2-$CH_3$—$C_6H_4$ | —CH=CH— | E | | |
| 190 | 4-$CH_3$—$C_6H_4$ | —CH=CH— | E | | |
| 191 | 4-i-$C_3H_7$—$C_6H_4$ | —CH=CH— | E | | |
| 192 | 4-t-$C_4H_9$—$C_6H_4$ | —CH=CH— | E | | |
| 193 | 2-$OCH_3$—$C_6H_4$ | —CH=CH— | E | | |
| 194 | 3-$OCH_3$—$C_6H_4$ | —CH=CH— | E | | |
| 195 | 4-$OCH_3$—$C_6H_4$ | —CH=CH— | E | | |
| 196 | 2-phenoxy-$C_6H_4$ | —CH=CH— | E | | |
| 197 | 3-phenoxy-$C_6H_4$ | —CH=CH— | E | | |
| 198 | 4-phenoxy-$C_6H_4$ | —CH=CH— | E | | |
| 199 | $C_6H_5$ | —$(CH_2)_3$— | E | | |
| 200 | $C_6H_5$ | —$(CH_3)$—$CH_2$—$CH_2$— | E | | |
| 201 | $C_6H_5$ | —$CH_2$—$CH(CH_3)$—$CH_2$— | E | | |
| 202 | $C_6H_5$ | —$CH_2$—$CH_2$—$CH(CH_3)$— | E | | |
| 203 | 2-Cl—$C_6H_4$ | —$(CH_2)_3$— | E | | |
| 204 | 4-Cl—$C_6H_4$ | —$(CH_2)_3$— | E | | oil |
| 205 | 2-$OCH_3$—$C_6H_4$ | —$(CH_2)_3$— | E | | |
| 206 | 4-$OCH_3$—$C_6H_4$ | —$(CH_2)_3$— | E | | |
| 207 | 4-t-$C_4H_9$—$C_6H_4$ | —$(CH_2)_3$— | E | | |
| 208 | $C_6H_5$ | —CH=CH—$CH_2$— | E | 3.28(d,2H); 3.73(s,3H); 3.83(s,3H); 5.17(s,2H); 6.33(m,1H); 6.52(d,1H); 7.33(m,9H); 7.62(s,1H). | oil |
| 209 | $C_6H_5$ | —$(CH_2)_4$— | E | 1.65(m,4H); 2.35(t,2H); 2.60(t,2H); 3.65(s,3H); 3.70(s,3H); 5.03(s,2H); 7.29(m,9H); 7.53(s,1H). | oil |
| 210 | 2-Cl—$C_6H_4$ | —$(CH_2)_4$— | E | | |
| 211 | 4-Cl—$C_6H_4$ | —$(CH_2)_4$— | E | | |
| 212 | 2-$OCH_3$—$C_6H_4$ | —$(CH_2)_4$— | E | | |
| 213 | 4-$OCH_3$—$C_6H_4$ | —$(CH_2)_4$— | E | | |
| 214 | 4-$CF_3$—$C_6H_4$ | —$(CH_2)_4$— | E | | oil |
| 215 | 2-$CH_3$—$C_6H_4$ | —$(CH_2)_4$— | E | | |
| 216 | 4-$CH_3$—$C_6H_4$ | —$(CH_2)_4$— | E | | |
| 217 | $C_6H_5$ | —$CH_2$—$CH_2$—$CH(CH_3)$—$CH_2$— | E | | |
| 218 | $C_6H_5$ | —$(CH_2)_5$— | E | | oil |
| 219 | 2-$CH_3$—$C_6H_4$ | —$(CH_2)_5$— | E | | |
| 220 | 4-$CH_3$—$C_6H_4$ | —$(CH_2)_5$— | E | | |
| 221 | 2-Cl—$C_6H_4$ | —$(CH_2)_5$— | E | | |
| 222 | 4-Cl—$C_6H_4$ | —$(CH_2)_5$— | E | | |

TABLE 1-continued

Compounds of the formula I ($R^1 = OCH_3$, $R_2 = CO_2CH_3$)
The configuration statement relates to the β-methoxyacrylate group

| No. | $R^3$ | $(X)_n$ | Configuration | $^1$H-NMR data (CDd$_3$), δ in [ppm] | m.p. (°C.) |
|---|---|---|---|---|---|
| 223 | 2-OCH$_3$—C$_6$H$_4$ | —(CH$_2$)$_5$— | E | | |
| 224 | 4-OCH$_3$—C$_6$H$_4$ | —(CH$_2$)$_5$— | E | | |
| 225 | 4-CF$_3$—C$_6$H$_4$ | —(CH$_2$)$_5$— | E | | |
| 226 | C$_6$H$_5$ | —CH$_2$—CH$_2$—CH$_2$—CH(CH$_3$)—CH$_2$— | E | 0.95(d,3H); 1.25(m,1H); 1.37(m,1H); 1.63(m,2H); 2.00(m,1H); 2.13(m,1H); 2.32(m,1H); 2.57(m,2H); 3.67(s,3H); 3.75(s,3H); 5.03(s,2H); 7.29(m,9H); 7.56(s,H). | oil |
| 227 | C$_6$H$_5$ | —CH$_2$—CH(CH$_3$)—CH$_2$—CH(CH$_3$)—CH$_2$— | E | | |
| 228 | 4-t-C$_4$H$_9$—C$_6$H$_4$ | —CH$_2$—CH(CH$_3$)—CH$_2$—CH(CH$_3$)—CH$_2$— | E | 0.83, 0.88, 0.96(3d,6H); 1.19(m,2H); 1.31(s,9H); 1.79(m,1H); 2.20(m,4H); 2.60(m,1H); 3.69(s,3H); 3.81(s,3H); 5.03(s,2H); 7.25(m,8H); 7.57(s,1H). | oil |
| 229 | C$_6$H$_5$ | —(CH$_2$)$_6$— | E | | |
| 230 | C$_6$H$_5$ | —(CH$_2$)$_4$—CH(CH$_3$)—CH$_2$— | E | | |
| 231 | C$_6$H$_5$—O— | —CH$_2$— | E | | |
| 232 | 2-Cl—C$_6$H$_4$—O— | —CH$_2$— | E | | |
| 233 | 3-Cl—C$_6$H$_4$—O— | —CH$_2$— | E | | |
| 234 | 4-Cl—C$_6$H$_4$—O— | —CH$_2$— | E | | |
| 235 | 2,4-Cl$_2$—C$_6$H$_3$—O— | —CH$_2$— | E | | |
| 236 | 2-CH$_3$—C$_6$H$_4$—O— | —CH$_2$— | E | | |
| 237 | 4-CH$_3$—C$_6$H$_4$—O— | —CH$_2$— | E | | |
| 238 | 2-OCH$_3$—C$_6$H$_4$—O— | —CH$_2$— | E | | |
| 239 | 4-OCH$_3$—C$_6$H$_4$—O— | —CH$_2$— | E | | |
| 240 | 4-CF$_3$—C$_6$H$_4$—O— | —CH$_2$— | E | | |
| 241 | C$_6$H$_5$—O— | —CH(CH$_3$)— | E | | |
| 242 | C$_6$H$_5$—O— | —CH$_2$—CH$_2$— | E | | |
| 243 | 2-Cl—C$_6$H$_4$—O— | —CH$_2$—CH$_2$— | E | | |
| 244 | 4-Cl—C$_6$H$_4$—O— | —CH$_2$—CH$_2$— | E | | |
| 245 | 2-CH$_3$—C$_6$H$_4$—O— | —CH$_2$—CH$_2$— | E | | |
| 246 | 4-CH$_3$—C$_6$H$_4$—O— | —CH$_2$—CH$_2$— | E | | |
| 247 | 2-OCH$_3$—C$_6$H$_4$—O— | —CH$_2$—CH$_2$— | E | | |
| 248 | 4-OCH$_3$—C$_6$H$_4$—O— | —CH$_2$—CH$_2$— | E | | |
| 249 | 4-t-C$_4$H$_9$—C$_6$H$_4$—O— | —CH$_2$—CH$_2$— | E | | |
| 250 | 4-sec.-C$_4$H$_9$—C$_6$H$_4$—O— | —CH$_2$—CH$_2$— | E | | |
| 251 | C$_6$H$_5$—O— | —(CH$_2$)$_3$— | E | | |
| 252 | 2-Cl—C$_6$H$_4$—O— | —(CH$_2$)$_3$— | E | | |
| 253 | 4-Cl—C$_6$H$_4$—O— | —(CH$_2$)$_3$— | E | | |
| 254 | 3-F—C$_6$H$_4$—O— | —(CH$_2$)$_3$— | E | | |
| 255 | 4-F—C$_6$H$_4$—O— | —(CH$_2$)$_3$— | E | | |
| 256 | 2-CH$_3$—C$_6$H$_4$—O— | —(CH$_2$)$_3$— | E | | |
| 257 | 4-CH$_3$—C$_6$H$_4$—O— | —(CH$_2$)$_3$— | E | | |
| 258 | 2-OCH$_3$—C$_6$H$_4$—O— | —(CH$_2$)$_3$— | E | | |
| 259 | 4-OCH$_3$—C$_6$H$_4$—O— | —(CH$_2$)$_3$— | E | | |
| 260 | 2,4-Cl$_2$—C$_6$H$_3$—O— | —(CH$_2$)$_3$— | E | | |
| 261 | 4-Cl—C$_6$H$_4$—O— | —CH(CH$_3$)—CH$_2$—CH$_2$— | E | | |

TABLE 1-continued

Compounds of the formula I ($R^1$ = $OCH_3$, $R^2$ = $CO_2CH_3$)
The configuration statement relates to the β-methoxyacrylate group

| No. | $R^3$ | $(X)_n$ | Configuration | $^1$H-NMR data (CDd$_3$), δ in [ppm] | m.p. (°C.) |
|---|---|---|---|---|---|
| 262 | 2-CF$_3$—C$_6$H$_4$—O— | —(CH$_2$)$_3$— | E | | |
| 263 | 3-CF$_3$—C$_6$H$_4$—O— | —(CH$_2$)$_3$— | E | | |
| 264 | 4-CF$_3$—C$_6$H$_4$—O— | —(CH$_2$)$_3$— | E | | |
| 265 | 4-t-butoxy-C$_6$H$_4$—O— | —(CH$_2$)$_3$— | E | | |
| 266 | 2-CH$_3$,4-Cl—C$_6$H$_3$—O— | —(CH$_2$)$_3$— | E | | |
| 267 | 4-C$_2$H$_5$—C$_6$H$_4$—O— | —(CH$_2$)$_3$— | E | | |
| 268 | 4-iso-C$_3$H$_7$—C$_6$H$_4$—O— | —(CH$_2$)$_3$— | E | | |
| 269 | 4-t-C$_4$H$_9$—C$_6$H$_4$—O— | —(CH$_2$)$_3$— | E | | |
| 270 | C$_6$H$_5$—O— | —CH$_2$—CH(CH$_3$)—CH$_2$— | E | | |
| 271 | C$_6$H$_5$—O— | —(CH$_2$)$_4$— | E | 1.88(m,4H); 2.45(t,2H); 3.74(s,3H); 3.88(s,3H); 4.01(t,2H); 5.09(s,2H); 7.18(m,9H); 7.64(s,1H). | oil |
| 272 | 2-Cl—C$_6$H$_4$—O— | —(CH$_2$)$_4$— | E | | |
| 273 | 4-Cl—C$_6$H$_4$—O— | —(CH$_2$)$_4$— | E | | |
| 274 | 2,4-Cl$_2$—C$_6$H$_3$—O— | —(CH$_2$)$_4$— | E | | |
| 275 | 2,6-Cl$_2$—C$_6$H$_3$—O— | —(CH$_2$)$_4$— | E | | |
| 276 | 2-CH$_3$—C$_6$H$_4$—O— | —(CH$_2$)$_4$— | E | | |
| 277 | 4-CH$_3$—C$_6$H$_4$—O— | —(CH$_2$)$_4$— | E | | |
| 278 | C$_6$H$_5$—O— | —CH$_2$—CH$_2$—CH(CH$_3$)—CH$_2$— | E | | |
| 279 | C$_6$H$_5$—O— | —(CH$_2$)$_5$— | E | | |
| 280 | 3-Cl—C$_6$H$_4$—O— | —(CH$_2$)$_5$— | E | | |
| 281 | C$_6$H$_5$—O— | —(CH$_2$)$_3$—CH(CH$_3$)—CH$_2$— | E | | |
| 282 | C$_6$H$_5$—O— | —(CH$_2$)$_6$— | E | | |
| 283 | 3-Cl—C$_6$H$_5$—O— | —(CH$_2$)$_6$— | E | | |
| 284 | C$_6$H$_5$—O— | —(CH$_2$)$_4$—CH(CH$_3$)—CH$_2$— | E | | |
| 285 | A 1* | — | E | 1.13, 1.18, 1.25, 1.30(4s,6H); 1.73 (s,6H); 1.88, 2.08(2m,1H); 3.70 (s,3H); 3.82(s,3H); 4.90, 5.45(2m,1H); 5.05(m,2H); 7.38(m,H); 7.62(s,1H). | oil |
| 286 | A 2* | — | E | 1.88, 1.23, 1.27, 1.30(4s,6H); 1.13, 1.88 (2d,1H); 2.03, 2.27(2m,1H); 3.70 (s,3H); 3.82(s,3H); 5.03(m,2H) 5.62, 6.30(2d,1H); 7.35(m,4H); 7.70(s,1H). | oil |
| 287 | A 3* | — | E | 1.19, 1.24, 1.28, 1.31(4s,6H); 1.68, 1.88 (2d,1H); 1.96, 2.19(2m,1H); 3.72 (s,3H); 3.83(s,3H); 5.04(m,2H); 6.16, 6.81(2d,1H); 7.32(m,4H); 7.60(s,1H). | oil |
| 288 | A 4* | — | E | 1.24, 1.29, 1.32, 1.35(4s,6H); 1.79, 2.00(2d,1H); 2.17, 2.44,(2m,1H); 3.71(s,3H); 3.83(s,3H); 5.07 (m,2H); 6.16, 6.97(2d,1H); 7.36(m,4H); 7.60(s,1H). | oil |
| 289 | A 5* | — | E | 1.45, 1.49(2s,6H); 2.13(s,1H); 3.73(s,3H); 3.84(s,3H); 5.09(s,2H); 7.36(m,4H); 7.60(s,1H). | oil |
| 290 | A 6* | — | E | | |
| 291 | A 7* | — | E | | |
| 292 | A 8* | — | E | | |

TABLE 1-continued

Compounds of the formula I ($R^1$ = $OCH_3$, $R_2$ = $CO_2CH_3$)
The configuration statement relates to the β-methoxyacrylate group

| No. | $R^3$ | $(X)_n$ | Configuration | $^1$H-NMR data (CDd$_3$), δ in [ppm] | m.p. (°C.) |
|---|---|---|---|---|---|
| 293 | A 9* | — | E | | |
| 294 | A 10* | — | E | | |
| 295 | A 11* | — | E | | |
| 296 | A 12* | — | E | | |
| 297 | A 13* | — | E | | |
| 298 | A 14* | — | E | | |
| 299 | A 15* | — | E | | |
| 300 | 2-furyl | —CH=CH— | E | | oil |
| 301 | N-pyrrolyl | CH(iso-$C_3H_7$) | E | 0.77(d,3H); 0.98(d,3H); 2.42(sept.,1H); 3.69(s,3H); 3.80(s,3H); 4.18(d,1H); 5.03(s,2H); 6.20(m,2H); 6.83(m,2H); 7.31(m,4H); 7.58(s,1H). | oil |
| 302 | 4-tert.-butyl-$C_6H_4$ | —$CH_2$—C($CH_3$)=CH—CH=CH— | E | 1.33(s,9H); 2.22(s,3H); 3.43(s,2H); 3.72(s,3H); 3.87(s,3H); 5.13(s,2H); 5.88(d,1H); 6.10(m,1H); 6.45(d,1H); 7.35(m,8H); 7.63(s,1H). | oil |
| 303 | H | —$CH_2$—CH($CH_3$)—$CH_2$—CH($CH_3$)— | E | 0.89(m,9H); 1.25(m,1H); 1.59(m,4H); 2.41(m,1H); 3.71(s,3H); 3.84(s,3H); 5.03(s,2H); 7.36(m,4H); 7.59(s,1H). | oil |
| 304 | H | —$CH_2$—CH($CH_3$)—$CH_2$—CH($CH_2C_2H_5$)— | E | | oil |
| 305 | H | —$CH_2$—CH($CH_3$)—$CH_2$—$CH_2$—CH(n-$C_3H_7$)— | E | | oil |
| 306 | H | —$CH_2$—CH($CH_3$)—$CH_2$—$CH_2$—CH(i-$C_3H_7$)— | E | | oil |
| 307 | H | —$CH_2$—C($CH_3$)$_2$—$CH_2$—CH($CH_3$)—$CH_2$— | E | | oil |
| 308 | H | —($CH_2$)$_3$—CH($C_2H_5$)— | E | | oil |
| 309 | H | —($CH_2$)$_5$—CH(n-$C_3$—$H_7$)— | E | | oil |
| 354 | H | —$CH_2$—O—$CH_2$—C($CH_3$)$_2$— | E | | oil |
| 355 | H | —($CH_2$)$_4$—O—$CH_2$—C($CH_3$)$_2$— | E | | oil |
| 356 | 1-methylcyclohexyl | —CHCl— | E | | oil |
| 357 | 4-Cl—$C_6H_4$ | —C($CH_3$)$_2$— | E | | oil |
| 358 | 4-Cl—$C_6H_4$ | —CH=CH—($CH_2$)$_4$ | E | | oil |
| 359 | $C_6H_5$ | — | E | | oil |
| 360 | 1-methylcyclopropyl | — | E | 0.65(m,2H); 1.22(m,2H); 1.30(s,3H); 3.70(s,3H); 3.83(s,3H); 5.00(s,2H); 7.14–7.48(m,4H); 7.60(s,1H). | oil |
| 361 | 2-methylcyclopropyl | — | E | | oil |
| 362 | 2,2-dichlorocyclopropyl | — | E | | oil |
| 363 | 1-methyl-2,2-dichlorocyclopropyl | — | E | | oil |
| 364 | 2-phenyl-cyclopropyl | — | E | | 106–108 |
| 365 | 1-phenylcyclopropyl | — | E | | 100–101 |
| 366 | 1-(2'-chlorophenyl)-cyclopropyl | — | E | 1.21(m,2H); 1.76(m,2H); 3.68(s,3H); 3.77(s,3H); 5.00(s,2H); 7.08–7.40 (m,8H); 7.55(s,1H). | |
| 367 | 1-(3'-chlorophenyl)-cyclopropyl | — | E | | oil |
| 368 | 1-(4'-chlorophenyl)-cyclopropyl | — | E | | oil |

TABLE 1-continued

Compounds of the formula I ($R^1$ = $OCH_3$, $R_2$ = $CO_2CH_3$)
The configuration statement relates to the β-methoxyacrylate group

| No. | $R^3$ | $(X)_n$ | Configuration | $^1$H-NMR data ($CD_3$), δ in [ppm] | m.p. (°C.) |
|---|---|---|---|---|---|
| 369 | 1-(2',4'-dichlorophenyl)-cyclopropyl | — | E | | |
| 370 | 1-(2',6'-dichlorophenyl)-cyclopropyl | — | E | | |
| 371 | 1-(3',4'-dichlorophenyl)-cyclopropyl | — | E | | |
| 372 | 1-(2'-fluorophenyl)-cyclopropyl | — | E | | |
| 373 | 1-(3'-fluorophenyl)-cyclopropyl | — | E | | |
| 374 | 1-(4'-fluorophenyl)-cyclopropyl | — | E | | |
| 375 | 1-(4'-bromophenyl)-cyclopropyl | — | E | | |
| 376 | 1-(2'-methylphenyl)-cyclopropyl | — | E | | |
| 377 | 1-(3'-methylphenyl)-cyclopropyl | — | E | | |
| 378 | 1-(4'-methylphenyl)-cyclopropyl | — | E | | |
| 379 | 1-(3',4'-dimethylphenyl)-cyclopropyl | — | E | | |
| 380 | 1-(4'-tert-Butylphenyl)-cyclopropyl | — | E | | |
| 381 | 1-(3'-trifluormethylphenyl)-cyclopropyl | — | E | | |
| 382 | 1-(2'-methoxyphenyl)-cyclopropyl | — | E | | |
| 383 | 1-(3'-methoxyphenyl)-cyclopropyl | — | E | | |
| 384 | 1-(4'-methoxyphenyl)-cyclopropyl | — | E | | 84–85 |
| 385 | 1-(2',4'-dimethoxyphenyl)-cyclopropyl | — | E | | |
| 386 | 1-(2',6'-dimethoxyphenyl)-cyclopropyl | — | E | | |
| 387 | 1-(3',4'-dimethoxyphenyl)-cyclopropyl | — | E | | |
| 388 | 1-(3',4'-dimethoxyphenyl)-cyclopropyl | — | E | | |

*The formulae are given in the text above The NMR data show the chemical shift (δ) of the protons in ppm in relation to tetramethylsilane. The solvent employed is $CDCl_3$.

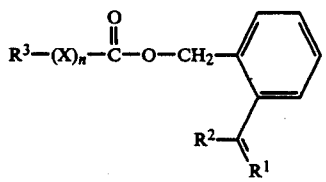

I

Erysiphe cichoracearum and Sphaerotheca fuliginea in cucurbits,
Podosphaera leucotricha in apples,
Uncinula necator in vines,
Puccinia species in cereals,
Rhizotonia solani in cotton,
Ustilago species in cereals and sugar cane,
Venturi inaequalis (scab) in apples,
Helminthosporium species in cereals,

TABLE 2

Compounds of the formula I

| No. | $R^1$ | $R^2$ | $R^3$ | $(X)_n$ | Configuration | m.p. (°C.) |
|---|---|---|---|---|---|---|
| 310 | OCH$_3$ | CN | H | —(CH$_2$)$_4$—CH(CH$_3$)—CH$_2$— | E | |
| 311 | OCH$_3$ | CN | C$_6$H$_5$ | —(CH$_2$)$_3$—CH(CH$_3$)—CH$_2$— | E | |
| 312 | OCH$_3$ | CN | A$_2$* | — | E/Z | oil |
| 313 | OCH$_3$ | CONH$_2$ | H | —(CH$_2$)$_4$—CH(CH$_3$)—CH$_2$— | E | |
| 314 | OCH$_3$ | CONH$_2$ | C$_6$H$_5$ | —(CH$_2$)$_3$—CH(CH$_3$)—CH$_2$— | E | |
| 315 | OCH$_3$ | CONH$_2$ | A$_2$* | — | E | |
| 316 | SCH$_3$ | CO$_2$CH$_3$ | H | —(CH$_2$)$_4$—CH(CH$_3$)—CH$_2$— | E | |
| 317 | SCH$_3$ | CO$_2$CH$_3$ | C$_6$H$_5$ | —(CH$_2$)$_3$—CH(CH$_3$)—CH$_2$— | E | |
| 318 | SCH$_3$ | CO$_2$CH$_3$ | A$_2$* | — | E | |
| 319 | SCH$_3$ | CN | H | —(CH$_2$)$_4$—CH(CH$_3$)—CH$_2$— | E | |
| 320 | SCH$_3$ | CN | C$_6$H$_5$ | —(CH$_2$)$_4$—CH(CH$_3$)—CH$_2$— | E | |
| 321 | SCH$_3$ | CN | A$_2$* | — | E | |
| 322 | SCH$_3$ | CONH$_2$ | H | —(CH$_2$)$_4$—CH(CH$_3$)—CH$_2$— | E | |
| 323 | SCH$_3$ | CONH$_2$ | C$_6$H$_5$ | —(CH$_2$)$_3$—CH(CH$_3$)—CH$_2$— | E | |
| 324 | SCH$_3$ | CONH$_2$ | A$_2$* | — | E | |
| 325 | Cl | CO$_2$CH$_3$ | H | —(CH$_2$)$_4$—CH(CH$_3$)—CH$_2$— | E | |
| 326 | Cl | CO$_2$CH$_3$ | C$_6$H$_5$ | —(CH$_2$)$_3$—CH(CH$_3$)—CH$_2$— | E | |
| 327 | Cl | CO$_2$CH$_3$ | A$_2$* | — | E | |
| 328 | Cl | CN | H | —(CH$_2$)$_4$—CH(CH$_3$)—CH$_2$— | E | |
| 329 | Cl | CN | C$_6$H$_5$ | —(CH$_2$)$_3$—CH(CH$_3$)—CH$_2$— | E | |
| 330 | Cl | CN | A$_2$* | — | E | |
| 331 | Cl | CONH$_2$ | H | —(CH$_2$)$_4$—CH(CH$_3$)—CH$_2$— | E | |
| 332 | Cl | CONH$_2$ | C$_6$H$_5$ | —(CH$_2$)$_3$—CH(CH$_3$)—CH$_2$— | E | |
| 333 | Cl | CONH$_2$ | A$_2$* | — | E | |
| 334 | N(CH$_3$)$_2$ | CO$_2$CH$_3$ | H | —(CH$_2$)$_4$—CH(CH$_3$)—CH$_2$— | E | |
| 335 | N(CH$_3$)$_2$ | CO$_2$CH$_3$ | C$_6$H$_5$ | —(CH$_2$)$_3$—CH(CH$_3$)—CH$_2$— | E | |
| 336 | N(CH$_3$)$_2$ | CO$_2$CH$_3$ | A$_2$* | — | E | |
| 337 | N(CH$_3$)$_2$ | CN | H | —(CH$_2$)$_4$—CH(CH$_3$)—CH$_2$— | E | |
| 338 | N(CH$_3$)$_2$ | CN | C$_6$H$_5$ | —(CH$_2$)$_3$—CH(CH$_3$)—CH$_2$— | E | |
| 339 | N(CH$_3$)$_2$ | CN | A$_2$* | — | E | |
| 340 | N(CH$_3$)$_2$ | CONH$_2$ | H | —(CH$_2$)$_4$—CH(CH$_3$)—CH$_2$— | E | |
| 341 | N(CH$_3$)$_2$ | CONH$_2$ | C$_6$H$_5$ | —(CH$_2$)$_4$—CH(CH$_3$)—CH$_2$— | E | |
| 342 | N(CH$_3$)$_2$ | CONH$_2$ | A$_2$* | — | E | |
| 343 | NHCH$_3$ | CO$_2$CH$_3$ | H | —CH$_2$)$_4$—CH(CH$_3$)—CH$_2$— | E | |
| 344 | NHCH$_3$ | CO$_2$CH$_3$ | C$_6$H$_5$ | —CH$_2$)$_4$—CH(CH$_3$)—CH$_2$— | E | |
| 345 | NHCH$_3$ | CO$_2$CH$_3$ | A$_2$* | — | E | |
| 346 | NHCH$_3$ | CN | H | —CH$_2$)$_4$—CH(CH$_3$)—CH$_2$— | E | |
| 347 | NHCH$_3$ | CN | C$_6$H$_5$ | —CH$_2$)$_4$—CH(CH$_3$)—CH$_2$— | E | |
| 348 | NHCH$_3$ | CN | A$_2$* | — | E | |
| 349 | NHCH$_3$ | CONH$_2$ | H | —CH$_2$)$_4$—CH(CH$_3$)—CH$_2$— | E | |
| 350 | NHCH$_3$ | CONH$_2$ | C$_6$H$_5$ | —CH$_2$)$_4$—CH(CH$_3$)—CH$_2$— | E | |
| 351 | NHCH$_3$ | CONH$_2$ | A$_2$* | — | E | |
| 352 | OCH$_3$ | CN | 2-F—C$_6$H$_4$ | — | E/Z | 64–65 |
| 353 | OCH$_3$ | CN | 1-methylcyclopropyl | — | E/Z | oil |

*The formulae are given in the text above.

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture and in vegetables such as cucumbers, beans and cucurbits.

The novel compounds are particularly useful for controlling the following plant diseases:
Erysiphe graminis in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifier and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), parafins (e.g., crude oil fractions), alcohols (e.g., methanol butanol), ketons (e.g., cyclohexanone), amines (e.g., ethanolamine dimethylformamide), and water; carriers such as ground natural minerals (e.g., kaoline, alumina, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylocellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., on *Paecilomyces variotii.*

The agents and the ready-to-use formulations prepared from them, such as solutions, emulsions, suspensions, powders, dusts, pastes and granules are applied in conventional manner, for example by spraying, atomizing, dusting, scattering, dressing or watering.

Examples for formulations are given below.

I. 90 parts by weight of compound no. 34 is mixed with 10 parts by weight of N-methyl-α-pyrrolidone. A mixture is obtained which is suitable for application in the form of very fine drops.

II. 20 parts by weight of compound no. 226 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylobenzenesulfonic acid, and 5 parts by weight of the adduct of 40 moles of ethylene oxide and 1 mole of castor oil. By pouring the solution into water and uniformly distributing it therein, an aqueous dispersion is obtained.

20 parts by weight of compound no. 286 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 289 is dissolved in a mixture consisting of 25 parts by weight of cyclohexanol, 65 parts by weight of a mineral oil fraction having a boiling point between 210° and 280° C., and 10 parts by weight of he adduct of 40 moles of ethylene oxide and 1 mole of castor oil. By pouring the solution into water and uniformly distributing it therein, an aqueous dispersion is obtained.

V. 80 parts by weight of compound no. 34 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquid is obtained.

VI. 3 parts by weight of compound no. 226 is intimately mixed with parts by weight of particulate kaolin. A dust is obtained containing 3% by weigh of the active ingredient.

30 parts by weight of compound no. 286 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 289 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 34 is intimately mixed with 2 parts by weight of the calcium salt of dodecylobenzenesulfonic acid, 8 parts by weight of a fatty alcohol polyglycol ether, 2 parts by weight of the sodium salt of phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:

sulfur,
dithiocarbamates and their derivatives, such as
ferric dimethldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propyloenebisdithioccarbamate and
N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethyloacrylate,
2-sec-butyl-4,6-dinitrophenyl isopropylocarbonate and
diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenylo-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole, 2-(fur-2-yl)-benzimidazole, 2-(thiazol-4-yl)benzimidazole,
N-(1,1,2,2-tetrachloroethylothio)-tetrahydrophthalimide,
N-trichloromethylthiotetrahydrophthalimide,
N-trichloromethylthiophthalimide,
N-dichlorofluoromethylothio-N'-N'-dimethyl-N-phenylosulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorphenylohydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilino-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylofuran-3-carboxamide,
N-cyclohexyl-N-methoxy-2,5-diethylfuran-3-carboxamide,
2-methylobenzanilide,
2-iodobenzanilide,
N-formyl-N-morpholine-2,2,2-trichloroethyloacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylomorpholine and its salts,
2,6-dimethyl-N-cyclododecylomorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylophenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylopyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl--2-oxycyclohexyl)2-hydroxyethyl]-glutaramide,
hexachloroenzene,
DL-methyl-N-(2,6-dimethylophenyl)-N-fur-2-yl alanate,
methyl DL-N-(2,6-dimethylphenyl)-N-2-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine -2,4-dione,
3-(3,5-dichlorophenyl)-1-isopropylcarbamylohydantoin,
N-(3,5-dichlorophenyl)-1,2-dimethylcyclopropane-1,2-dicarboximide,
2-cyano-[N-(ethyloaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylophenyl)-5-trifluoromethyl-3-chloro-2-aminopyridine, and
1-((bis-(4-fluorophenyl)-methylsilyl)-methyl)-1H-1,2,4-triazole.

USE EXAMPLES

The active ingredients used for comparison purposes were N-tridecyl-2,6-dimethylmorpholine (A) and α-(2-benzoylooxyphenyl)-β-methoxyacryloate (B)-disclosed in DE No. 1,164,152 and EP No. 178,826.

USE EXAMPLE 1

Action on Wheat Brown Rust

Leaves of pot-grown wheat seedlings of the "Frühgold" variety were dusted with spores of brown rust (*Puccinia recondita*). The pots were then placed for 24 hours at 20° to 22° C. in a high-humidity (90–95%) chamber. During this period the spores germinated and the germ tubes penetrated the leaf tissue. The infected plants were then sprayed to runoff with aqueous liquors containing (dry basis) 80% of active ingredients and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredients 34, 192, 226, 286, 287, 289, 360, 361, 362, 363, 368 and 369, applied as 0.025 wt % spray liquors, had a better fungicidal action (90%) than prior art active ingredients A and B (50%).

USE EXAMPLE 2

Action on *Pyrenophora teres*

Barley seedlings of the "Igri" variety at the two-leaf stage were sprayed to runoff with aqueous suspensions containing (dry basis) 80% of active ingredient and 20% of emulsifier. After 24 hours, the plants were inoculated with a spore suspension of the fungus *Pyrenophora teres* and placed for 28 hours in a high-humidity climatic cabinet kept at 18° C. The plants were then cultivated for a further 5 days in the greenhouse at 20° to 22° C. and a relative humidity of 70%.

The results show that active ingredients 1, 4, 11, 28, 34, 35, 71, 73, 83, 98, 101, 109, 154, 169, 192, 226, 271, 285, 286, 287, 288, 289, 304, 306, 355, 360, 361, 361 and 368, applied as 0.05% spray liquors, had a better fungicidal action (90%) than prior art active ingredient A (50%).

USE EXAMPLE 3

Action on *Plasmopara viticola*

Leaves of potted vines of the Müller-Thurgau variety were sprayed with aqueous suspensions containing (dry basis) 80% of active ingredients and 20% of emulsifier.

To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20 to 30° C. To accelerate and intensity the sporangiophore discharge, the plants were then again placed in the moist chamber for 16 hours. The extent of fungus attack was then assessed on the undersides of the leaves.

The results show that active ingredients 4, 11, 23, 28, 32, 34, 35, 71, 73, 79, 81, 82, 83, 98, 101, 109, 154, 161, 169, 179, 192, 226, 271, 285, 286, 287, 288, 289, 304, 356, 357, 359, 360, 362, 363, 364, 368 and 369, applied as 0.5% spray liquors, had a better fungicidal action (90%) than prior art active ingredient A (50%).

We claim:

1. Ortho-substituted benzyl carboxylate of the general formula

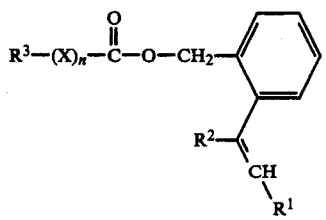

where $R^1$ is $C_1$–$C_4$-alkoxy, $C_1$–$C_4$-alkylthio, halogen or amino which is unsubstituted or mono- or disubstituted by $C_1$–$C_4$-alkyl, $R^2$ is $C_1$–$C_4$-alkoxycarbonyl, cyano or the group $CONH_2$, $R^3$ is hydrogen, halogen, cyano, aryl, aryloxy, the aromatic ring being unsubstituted or substituted by one or more of the following radicals: $C_1$–$C_6$-alkyl, $C_2$–$C_4$-alkenyl, $C_1$–$C_2$-haloalkyl, $C_1$–$C_6$-alkoxy, $C_1$–$C_4$-alkoxy-$C_1$–$C_4$-alkyl, aryl, aryl-$C_1$–$C_2$-alkyl, aryloxy, aryloxy-$C_1$–$C_4$-alkyl, aryloxy-$C_1$–$C_4$-alkoxy, haloaryloxy-$C_1$–$C_4$-alkoxy, halogen, halo-$C_1$–$C_4$-alkoxy, $C_1$–$C_4$-alkylthio, thiocyanato, cyano or nitro; or $R^3$ is a furyl or pyrrolyl radical, $C_3$–$C_7$-cycloalkyl, $C_5$–$C_6$-cycloalkenyl, adamantyl, fluorenyl or a substituted cyclopropyl radical which is substituted by methyl, halogen, $C_1$–$C_2$-haloalkyl, $C_3$–$C_4$-alkenyl, $C_2$–$C_4$-haloalkenyl, methoxycarbonyl-$C_3C_4$-alkenyl, cyclopentylidenemethyl, phenyl, halophenyl, $C_1C_2$-alkoxyphenyl or $C_1$–$C_4$-alkylphenyl, X is saturated or unsaturated $C_1$–$C_{12}$-alkylene which is unsubstituted or substituted by halogen or hydroxy, and n is 0 or 1.

2. A process for combating fungi, wherein the fungi or the materials plants, seed or the soil threatened by fungus attack are treated with a fungicidally effective amount of a compound of the formula

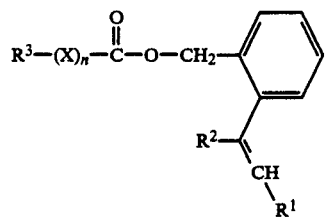

where $R^1$ is $C_1$–$C_4$-alkoxy, $C_1$–$C_4$-alkylthio, halogen or amino which is unsubstituted or mono- or disubstituted by $C_1$–$C_4$-alkyl, $R^2$ is $C_1$–$C_4$-alkoxycarbonyl, cyano or the group $CONH_2$, $R^3$ is hydrogen, halogen, cyano, aryl, aryloxy, the aromatic ring being unsubstituted or substituted by one or more of the following radicals: $C_1$–$C_6$-alkyl, $C_2$–$C_4$-alkenyl, $C_1$–$C_2$-haloalokyl, $C_1$–$C_6$-alkoxy, $C_1$–$C_4$-alkoxy-$C_1$–$C_4$-alkyl, aryl, aryl-$C_1$–$C_2$-alkyl, aryloxy, aryloxy-$C_1$–$C_4$-alkyl, aryloxy-$C_1$–$C_4$-alkoxy, haloaryloxy-$C_1$–$C_4$-alkoxy, halogen, halo-$C_1$–$C_4$-alkoxy, $C_1$–$C_4$-alkylthio, thiocyanato, cyano or nitro; or $R^3$ is a furyl or pyrrolyl radical, $C_3$–$C_7$-cycloalkyl, $C_5$–$C_6$-cycloalkenyl, adamantyl, fluorenyl or a substituted cyclopropyl radical which is substituted by methyl, halogen, $C_1$–$C_2$-haloalkyl, $C_3$–$C_4$-alkenyl, $C_2$–$C_4$-haloalkenyl, methoxycarbonyl-$C_3C_4$-alkenyl, cyclopentylidenemethyl, phenyl, halophenyl, $C_1$–$C_2$-alkoxyphenyl or $C_1$–$C_4$-alkylphenyl, X is saturated or unsaturated $C_1$–$C_{12}$-alkylene which is unsubstituted or substituted by halogen or hydroxy, and n is 0 is 1.

3. A fungicide containing an inert carrier and a fungicidally effective amount of a compound of the formula

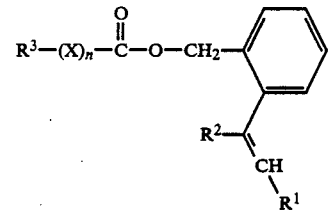

where $R^1$ is $C_1$–$C_4$-alkoxy, $C_1$–$C_4$-alkylthio, halogen or amino which is unsubstituted or mono- or disubstituted by $C_1$–$C_4$-alkyl, $R^2$ is $C_1$–$C_4$-alkoxycarbonyl, cyano or the group $CONH_2$, $R^3$ is hydrogen, halogen, cyano, aryl, aryloxy, the aromatic ring being unsubstituted or substituted by one or more of the following radicals: $C_1$–$C_6$-alkyl, $C_2$–$C_4$-alkenyl, $C_1$–$C_2$-haloalkyl, $C_1$–$C_6$-alkoxy, $C_1$–$C_4$-alkoxy-$C_1$–$C_4$-alkyl, aryl, aryl-$C_1C_2$-alkyl, aryloxy, aryloxy-$C_1$–$C_4$-alkyl, aryloxy-$C_1$–$C_4$-alokoxy, haloaryloxy-$C_1$–$C_4$-alkoxy, halogen, halo-$C_1$–$C_4$-alkoxy, $C_1$–$C_4$alkylthio, -thiocyanato, cyano or nitro; or $R^3$ is a furyl or pyrrolyl radical, $C_3$–$C_7$-cycloalkyl, $C_5$–$C_6$-cycloalkenyl, adamantyl, fluorenyl or a substituted cyclopropyl radical which is substituted by methyl, halogen, $C_1-C_2$-haloalkyl, $C_3-C_4$-alkenyl, $C_2-C_4$-haloalkenyl, methoxycarbonyl-$C_3C_4$-alkenyl, cyclopentylidenemethyl, phenyl, halophenyl, $C_1-C_2$-alkoxyphenyl or $C_1-C_4$-alkylphenyl, X is saturated or unsaturated $C_1-C_{12}$-alkylene which is unsubstituted or substituted by halogen or hydroxy, and n is 0 or 1.

4. A compound of the formula I as set forth in claim 1, wherein $R^3$ is hydrogen, $X_n$ is 2-methylpentylene, $R^1$ is methoxy $R^1$ and $R^2$ is methoxycarbonyl.

5. A compound of the formula I as set forth in claim 1, where $R^3$ is phenyl, $X_n$ is 2-methylpentylene, $R^1$ is methoxy and $R^2$ is methoxycarbonyl.

6. A compound of the formula as set forth in claim 1 where n is o, $R^1$ is methoxy, $R^2$ is methoxycarbonyl and $R^3$ is 1-methylcyclopropyl.

* * * * *